United States Patent [19]

Schammel

[11] Patent Number: 4,797,497

[45] Date of Patent: Jan. 10, 1989

[54] TRIMELLITIC ANHYDRIDE PURIFICATION PROCESS

[75] Inventor: Wayne P. Schammel, Naperville, Ill.

[73] Assignee: Amoco Corporation, Chicago, Ill.

[21] Appl. No.: 160,187

[22] Filed: Feb. 25, 1988

[51] Int. Cl.⁴ ............................................ C07D 307/89
[52] U.S. Cl. .................................................... 549/245
[58] Field of Search ......................................... 549/245

[56] References Cited

U.S. PATENT DOCUMENTS

| | | | |
|---|---|---|---|
| 2,971,011 | 2/1961 | Liao et al. | 549/245 |
| 3,161,658 | 12/1964 | Meyer | 549/245 |
| 4,587,350 | 5/1986 | Kilner et al. | 549/245 |

Primary Examiner—Richard L. Raymond
Attorney, Agent, or Firm—Gunar J. Blumberg; William H. Magidson; Ralph C. Medhurst

[57] ABSTRACT

A process for the purification of trimellitic anhydride is disclosed herein in which molten trimellitic anhydride is mixed with pseudocumene at a temperature of about 200° F. to about 450° F. and wherein the purified trimellitic anhydride is recovered by crystallization from the pseudocumene mother liquor. The recovered trimellitic anhydride is further washed and dried. Trimellitic anhydride is useful in the manufacture of amide imide resins and various polyester.

4 Claims, No Drawings

TRIMELLITIC ANHYDRIDE PURIFICATION PROCESS

BACKGROUND OF THE INVENTION

This invention relates to a process for the manufacture of trimellitic anhydride from pseudocumene and more particularly relates to a method of recovering pure trimellitic anhydride by a novel extraction process comprising the direct mixing of molten trimellitic anhydride at a temperature of about 350° F. to about 450° F. with pseudocumene; cooling the resulting mixture to produce crystalline trimellitic anhydride; separating crystalline trimellitic anhydride from mother liquor; washing the trimellitic anhydride and drying the crystalline trimellitic anhydride.

The process of this invention provides a commercial process for the manufacture of trimellitic anhydride through the catalytic liquid-phase oxidation of commercially available pseudocumene with air in the presence of acetic acid as a reaction solvent. The recrystallized trimellitic anhydride has better color properties than conventional trimellitic anhydride produced in the flaked form.

Pseudocumene is oxidized with air mainly to a mixture of dimethylbenzoic acids in the presence of catalysis provided only by cobalt and/or manganese oxidation catalysts under liquid-phase conditions using acetic acid as the reaction solvent. By the use of oxygen as oxidant and a combination of cobalt as metal oxidation catalyst and alpha-methylenic ketones as side chain oxidation initiator or promoter, pseudocumene is oxidized mainly to a mixture of 2-methylterephthalic acid and 4-methyl isophthalic acid in the presence of acetic acid solvent and under liquidphase conditions at atmospheric pressure. Catalytic liquid-phase oxidation of pseudocumene with air can be accomplished in the presence of acetic acid solvent and the catalysis provided by the combination of heavy metal oxidation catalyst and a source of bromine as disclosed and claimed in U.S. Pat. No. 2,833,816. This oxidation method using a combination of heavy metal oxidation catalyst and a source of bromine to provide catalysis describes the production of 92 weight percent trimellitic acid filter cake product in a two hour reaction at 198° C. (about 390° F.) The theoretical yield of trimellitic acid from pseudocumene is 175 weight percent. However, the oxidation method of U.S. Pat. No. 2,833,816 has been developed to produce total trimellitic acid yields in the range of 135 to 161 weight percent or about 77% to about 92% of theory based on the pseudocumene hydrocarbon feed. By total yield of trmmellitic acid is meant all of the trimellitic acid in the oxidation reaction effluent.

The more highly developed catalytic liquid phase air oxidation of pseudocumene by the method of U.S. Pat. No. 2,833,816 using the catalysis provided by the combination of heavy metal oxidation catalysts therein defined with bromine or a source of bromine under liquid-phase oxidation conditions produces total trimellitic acid yields of 135 to 161 weight percent based on commercially available pseudocumene. But, even then, there are also coproduced trimesic acid, iso- and terephthalic acids, 4-methylorthophthalic acid, 2-methyl-terephthalic acid, 4-methylisophthalic acid and formyl phthalic acids in amounts as to present substantial problems in the recovery of high quality trimellitic acid, dehydration of trimellitic acid to its intramolecular anhydride and recovery of that anhydride.

Another problem in the manufacture of trimellitic acid through the oxidation of pseudocumene to trimellitic acid in the presence of acetic acid comes from the relatively high solubility of trimellitic acid in acetic acid. This solubility goes from about 1.0 pound per 100 pounds glacial acetic acid at 80° F. to 6.5 pounds per 100 pounds glacial acetic acid at 220° F. The presence of water in the acetic acid increases the solubility of trimellitic acid so that in aqueous acetic acid solvent having 82 to 85% acetic acid, and 18 to 15% water by weight, there are dissolved at 80° and 220° F. about 3.2 pounds and 16.5 pounds trimellitic acid per 100 pounds solvent. Ordinarily, aqueous acetic acid of 90 to 98% (10 to 2% water) by weight is used in the oxidation as solvent not only because acetic acid of higher strength is more expensive to recover, but also because the presence of 2 to 10% water by weight substantially eliminates oxidation induction. During oxidation of the methyl groups, to carboxylic acid groups water is produced as a by-product and is generally retained through the removal of heat of reaction by condensing the acetic acid and water boil up from the liquid phase in the oxidation zone and returning the condensate to the oxidation zone. The aqueous acetic acid solvent in the effluent removed from the oxidation zone suitably contains about 10 to 25% water (90 to 75% acetic acid) by weight when the 90 to 98% aqueous acetic acid solvent is used in the weight ratios of 5 to 2 parts per part of pseudocumene. Thus, at usual crystallization temperatures of 60° to 120° F. a substantial amount of trimellitic acid remains in solution.

For example, in Example II of U.S. Pat. No. 3,161,658, there is described the cooling to 100° F. of an oxidation reaction effluent containing for each 500 parts acetic acid solvent, 200 parts trimellitic acid and 50 parts of pseudocumene oxidation intermediates. There was recovered 135 parts crystalline trimellitic acid per 500 parts of acetic acid solvent. Thus, of the originally produced 200 parts trimellitic acid, there was left in solution 65 parts or 32.5%. This appears to have been an oxidation of pseudocumene conducted in the presence of acetic acid solvent in the ratio of about 3.5 parts solvent per part of pseudocumene. Higher ratios of solvent to pseudocumene would have caused a greater proportion of the total trimellitic acid to remain in solution at 100° F. For example, at a 5 to 1 solvent ratio, 45% of the trimellitic acid produced would have remained in solution at crystallization and filtration temperatures of 100° F.

U.S. Pat. No. 3,161,658 provides one technique for recovering the trimellitic acid remaining dissolved in the aqueous acetic acid mother liquor. This is done by adding the mother liquor to a pool of molten trimellitic anhydride (370°–375° F.) and flashing off water and acetic acid vapors and drawing off from the molten pool liquid in an amount equivalent to the weight of solids charged with the mother liquor. This liquid draw-off is solidified, ground, and dissolved in a dialkyl ketone or aromatic hydrocarbon (the ketone solution must be filtered to remove insolubles) and the solution is combined with anhydride from dehydrated 100° F. filter cake. The aromatic hydrocarbon solution is filtered to remove an insoluble oily residue and the filtrate is cooled to 75° F. to precipitate trimellitic anhydride. This anhydride can be added to the anhydride from dehydration of the 100° F. first filter cake. By simple flashing at 6 mm Hg absolute, there is recovered a trimellitic anhydride product of 95% anhydride content, 95% pure in yields of 85 to 90% based on the trimellitic acid produced by the oxidation. However, the ketone and aromatic hydrocarbon solvents are flammable, and their foregoing uses, although advantageous, do present fire hazards.

Other problems in the recovery of trimellitic anhydride from trimellitic acid produced by catalytic liquid phase air oxidation in acetic acid solvent arises in the distillative and/or evaporative separation of trimellitic anhydride from the melt produced by dehydrating trimellitic acid. In this melt there is a substantial amount of iso- and terephthalic acids produced mainly as co-products of oxidation and some by decarboxylation of trimellitic acid when the dehydration is carried out at temperatures of 410° to 428° F. or higher. The literature reports that trimellitic acid is dehydrated to its anhydride at 216° C. (about 421° F.). But at 410° to 428° F. some decarboxylation takes place, not to produce phthalic anhydride only, but rather to produce mainly iso- and terephthalic acids. However, this decarboxylation can be substantially eliminated during dehydration by operating at about 335° to 400° F. with an inert gas sweep. This is disclosed and claimed in U.S. Pat. No. 2,971,011. The gas sweep is conducted with gas inert to trimellitic anhydride at 335° to 400° F. Nitrogen, flue gas, $CO_2$, hydrocarbon vapors and even steam can be used as inert gas.

Such gas sweep dehydration does not eliminate the problem caused by the presence of oxidation by-products iso- and terephthalic acids. When either or both of isophthalic acid and terephthalic acid are present in the molten trimellitic anhydride to be recovered by distillative and/or evaporative techniques, they are carried over with the trimellitic anhydride vapors after the amounts thereof in the molten anhydride bottoms reach their saturation concentrations. This, of course, adversely affects the clarity and purity of recovered molten trimellitic intramolecular anhydride and the reactivity of the anhydride. Our novel process eliminates this problem.

The intramolecular anhydride of trimellitic acid has become a commercial starting material for surface coatings having the desired properties of high thermal decomposition, high temperature insulating properties, good resistance to chemical attack and are substantially insoluble. These surface coatings are obtained from prepolymers prepared, for example, from trimellitic intramolecular anhydrides and polyamines. Because of the trifunctionality of the intramolecular anhydride, the final surface coating product is a polyimide-amide. The intramolecular anhydride of trimellitic acid also has become a starting material for solid foams obtained by reacting an isothiocyanate, among other reactants, with the intramolecular anhydride. Air and heat drying points and enamels with hydrocarbon or water solvent vehicles are also prepared from the intramolecular anhydride of trimellitic acid. For most of these uses, trimellitic acid intramolecular anhydride of an anhydride purity of 98 to 99% is required.

For many of the commercial applications mentioned above, color of the trimellitic anhydride has become an important specification. Highly colored brown, tan, or even yellow products may no longer be acceptable. Triethylene Glycol (TEG) color is a typical standard measure of this performance quality of trimellitic anhydride. In this method, a reaction of the trimellitic anhydride with a 300% molar excess of triethylene glycol is carried out at 500° F. (about 260° C.) to produce a solution whose color is matched instrumentally with APHA color standards. Reaction time is sixty minutes. A typical commercial product must have a TEG color of 170 or less.

U.S. Pat. No. 4,587,350, incorporated by reference herein, discloses a process for the oxidation of pseudocumene to trimellitic acid by a catalytic oxidation of pseudocumene with air in the presence of acetic acid in an oxidation zone in the liquid phase with catalysts comprising zirconium, cobalt, and manganese and a source of bromine.

The process of this invention provides for a purification process of trimellitic anhydride which meets the new strategic demands of the market.

The improvement arises by the direct mixing of hot pseudocumene, that is, pseudocumene heated to a temperature of about 350° F. to about 450° F. with molten trimellitic anhydride taken either from the dehydration section or the fractionator. The trimellitic anhydride dissolves in the pseudocumene. The resulting mixture is cooled to produce crystalline trimellitic anhydride. The crystalline trimellitic anhydride was suitably separated from the mother liquor by filtration, to be washed, dried, and bagged. The mother liquor is primarily pseudocumene and is suitably washed with either NaOH, KOH, CsOH or $Ca(OH)_2$ to recover trimellitic acid for recycle back to the dehydrators. The resultant pseudocumene is then recycled to the reactors where it is oxidized to trimellitic acid.

Accordingly, therefore, it is a principal objective of the present invention to provide the process for purifying trimellitic anhydride which overcomes the difficulties heretofore encountered and which simply, expeditiously, and inexpensively produces a purified trimellitic anhydride.

In accordance with the present invention, it has now been found that trimellitic anhydride was suitably purified by heating at a temperature of about 200° F. to about 450° F. and at ambient pressure for a period of about 10 to about 210 minutes crude trimellitic anhydride and crystallizing the purified trimellitic anhydride at a temperature of about 80° to about 400° F.

It has been found, surprisingly and unexpectedly, that the foregoing process overcomes the disadvantages of the prior art and enables the attainment of a purified trimellitic anhydride readily and inexpensively. The findings of the present invention are especially surprising in view of the fact that purification of a solid precipitated from a liquid cannot be usually effected by recrystallization from the feedstock.

My novel purification process is particularly applicable to a process for the manufacture of trimellitic acid anhydride and is conducted by the steps of catalytic oxidation of pseudocumene in the presence of acetic acid in an oxidation zone wherein liquid-phase conditions are maintained, and the catalyst comprises one or more heavy metal oxidation catalysts comprising zirconium, cobalt, manganese and a source of bromine. In this process, the oxidation reaction is cooled to crystallize trimellitic acid and trimellitic acid is separated and recovered from the acetic acid solvent mother liquor by distillation from the acetic acid mother liquor, thus obtaining a mixture of acetic acid and water for concentration of the acetic acid content to provide acetic acid solvent concentrate for recycle to the oxidation and to obtain a bottoms fraction having high melting solids. In this process the crystalline trimellitic acid is heated to convert it to its anhydride.

Desirable operating conditions for the process steps of this invention are given in the following description. Oxidation reaction effluent is obtained by the oxidation of pseudocumene with air in an oxidation zone at 320° to 410° F. and 140 to 370 psig in the presence of 2 to 3.5 parts inclusive of 90 to 98% aqueous acetic acid (10 to 2% water) per part of pseudocumene of 97 to 99.5% by weight purity in the presence of heavy metals (e.g. supplied as zirconium acetate, and cobalt and manganese acetate tetrahydrates) in a total concentration of 0.06 to 0.30 weight percent as metals and bromide as provided by hydrogen bromide, sodium bromide, and/or tetrabromoethane in a bromide concentration of 0.1 to 0.7 weight percent. The weight percent of catalyst components are based on the acetic acid solvent. The resulting oxidation effluent withdrawn from the oxidation zone is at 400° to 410° F. and contains trimellitic acid in an amount equivalent to 1.35 to 1.61 pounds per pound of pseudocumene and aromatic impurities in the range of 30 to 5 pounds per 100 pounds of trimellitic acid.

A slurry of trimellitic acid crystals of from 40 to 60% crystal solids by weight is obtained depending upon the portion of water and acetic acid vaporized and removed from a crystallization zone.

The slurry from the crystallization zone is continuously transferred to a rotary vacuum filter, centrifugal filter, or filter press and trimellitic acid crystal cake is separated at 110° to 130° F. The mother liquor is collected in a surge drum. The filter cake contains 15 to 35% acetic acid.

The acetic acid wet filter cake and recycle residue from the mother liquor stripper stillpot are continuously charged by screw conveyor to a boiler containing molten crude trimellitic anhydride at about 450° F. and pressures in a range of about 10 to 25 psia. The hold time in the boiler is about 1 to 2 hours which is sufficient time to assure removal of acetic acid and dehydrate about 85% of the feed trimellitic acid to its anhydride. Some of the anhydride tends to leave the top of the boiler with the acetic acid vapors. These vapors are transferred to the stripper feed vessel and combined with the mother liquor.

Liquid is withdrawn continuously from the first dehydration zone and fed into the second dehydration zone operated at a temperature in the range of about 450° to 500° F. and at a pressure of about 100 to about 400 mm. Hg. The hold time in the second dehydration zone is about 1 to 2 hours to complete conversion of the trimellitic acid to its anhydride.

Liquid is withdrawn continuously from the second dehydration boiler in an amount equivalent in weight to the dry solids content of the wet cake fed to the boiler. This liquid contains crude trimellitic anhydride (3 to 5% impurities). Molten pseudocumene is charged to it at a temperature of about 200° F. to about 450° F. The liquid anhydride is crystallized from the molten pseudocumene by cooling the mixture to a temperature in the range of about 80° F. to about 150° F. at about 100 to about 760 mm. Hg absolute pressure.

In the process of this invention, the crude and molten trimellitic anhydride is mixed with pseudocumene. This mixture is then cooled and purified trimellitic anhydride is recovered by crystallization. The solid, purified trimellitic anhydride is recovered from the mother liquor by filtration. The recovered trimellitic anhydride is washed and dried.

Our process is particularly useful since pseudocumene subjected to oxidation conditioning is suitably treated by caustic or water wash to remove trimellitic anhydride. The aqueous phase containing trimellitic anhydride is suitably recycled to the dehydrator to minimize loss of trimellitic anhydride. In our process the color of trimellitic anhydride is superior to that in the prior art and less trimellitic anhydride dust is formed.

The following examples illustrate the operation of our novel process.

EXAMPLE 1

50 grams of trimellitic anhydride and 150 grams of pseudocumene were put in a three neck round bottom flask with a water cooled condenser and a small nitrogen purge. The slurry was heated to the reflux temperature of pseudocumene (170° C.) and kept there for one hour. At this temperature the trimellitic anhydride totally dissolves and the solution takes on a yellow color. The solution was cooled to near room temperature (85° F.) and the resultant crystals of trimellitic anhydride were filtered, washed with more pseudocumene and hexane, and dried in a vacuum over overnight at about 60° C.

EXAMPLE 2

This extraction was performed as described in Example but at 170° C. the solution was hot filtered through celite and carbon. The solution was again cooled, filtered, and washed in the same manner as Example 1.

EXAMPLE 3

The following example is summarized in Table 1, wherein the purification is conducted as in Example 1, except that different operation separation temperatures have been used.

TABLE 1

| Trimellitic Anhydride | Pseudocumene Extraction of Trimellitic Anhydride | | | | |
|---|---|---|---|---|---|
| | No Extraction | 90° C. - 1 hr. | 115° C. - 1 hr. | 170° C. - 1 hr. | 170° C. - 1 hr.[2] |
| Phthalic anhydride, wt % | 0.17 | 0.06 | 0.01 | 0.01 | 0 |
| Terephthalic acid, wt % | 0.40 | 0.44 | 0.46 | 0.33 | 0.22 |
| Isophthalic acid, wt % | 0.34 | 0.35 | 0.32 | 0.21 | 0.25 |
| High Boiling, wt % | 0.61 | 0.38 | 0.25 | 0.04 | 0.15 |
| Bromine, ppm | 118 | 104 | 37 | 34 | 29 |
| Δ E[1] | 5.1 | — | 2.0 | — | 1.6 |

[1]Spectrophotometric technique used for detecting color in trimellitic anhydride samples
[2]Run included hot filtration of dissolved trimellitic anhydride

I claim:
1. A process for purifying trimellitic anhydride prepared by the oxidation of a reaction mixture comprising a dilute solution of pseudocumene in a lower fatty acid having two to four carbon atoms containing minor portions of water which comprise the direct mixing of the molten trimellitic anhydride with pseudocumene at a temperature of about 200° F. to about 450° F. to dissolve said molten trimellitic anhydride in said pseudocumene for a period of about 10 to about 210 minutes and crystallizing the purified trimellitic anhydride at a temperature of about 80° F. to about 400° F. and then cooling the resulting mixture to produce crystalline trimellitic anhydride from the pseudocumene.

2. The process of claim 1 wherein the reaction mixture is cooled to about 450° F. to about 100° F.

3. The process of claim 2 wherein the crystalline trimellitic anhydride is separated from pseudocumene by filtration.

4. The process of claim 1 wherein the lower fatty acid is acetic acid.

UNITED STATES PATENT AND TRADEMARK OFFICE
CERTIFICATE OF CORRECTION

PATENT NO. : 4,797,497
DATED : January 10, 1989
INVENTOR(S) : Wayne P. Schammel

It is certified that error appears in the above-identified patent and that said Letters Patent is hereby corrected as shown below:

| Column | Line | |
|--------|------|---|
| 1 | 36 | "liquidphase" should read --liquid-phase-- |
| 1 | 53 | "trmmellitic" should read --trimellitic-- |
| 3 | 28 | "$CO_z$," should read --$CO_2$,-- |

Signed and Sealed this

Eleventh Day of July, 1989

Attest:

DONALD J. QUIGG

Attesting Officer

Commissioner of Patents and Trademarks